US00PP13639P29

(12) United States Plant Patent
Uchneat

(10) Patent No.: US PP13,639 P2
(45) Date of Patent: Mar. 11, 2003

(54) DOUBLE IMPATIENS PLANT NAMED 'BALOLESTOP'

(75) Inventor: Michael S. Uchneat, St. Charles, IL (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/115,051

(22) Filed: Apr. 1, 2002

(51) Int. Cl.[7] ..... A01H 5/00
(52) U.S. Cl. ..... Plt./317
(58) Field of Search ..... Plt./317

(56) References Cited

U.S. PATENT DOCUMENTS 5,986,188 A * 11/1999 Leue ..... 800/323

OTHER PUBLICATIONS

UPOV ROM GTITM Computer Database, GTI JOUVE retrieval software, citation for 'Balolestop' 2002/02.*

* cited by examiner

*Primary Examiner*—Brian R. Campell
*Assistant Examiner*—W C Haas
(74) *Attorney, Agent, or Firm*—C. A. Whealy

(57) ABSTRACT

A new and distinct cultivar of Double Impatiens plant named 'Balolestop', characterized by its compact, upright, outwardly spreading and mounded plant habit; freely branching growth habit; dark green-colored leaves; freely flowering habit; and red purple and white bi-colored flowers that are fully double and positioned above the foliage.

1 Drawing Sheet

BOTANICAL CLASSIFICATION/CULTIVAR DESIGNATION

*Impatiens walleriana* cultivar Balolestop.

BACKGROUND OF THE INVENTION

The present Invention relates to a new and distinct cultivar of Double Impatiens plant, botanically known as *Impatiens walleriana*, and hereinafter referred to by the name 'Balolestop'.

The new Impatiens is a product of a planned breeding program conducted by the Inventor in Elburn, Ill. The objective of the breeding program was to develop new compact Double Impatiens cultivars with fully double flowers, freely branching growth habit, and attractive flower and foliage coloration.

The new Impatiens originated from a cross made by the Inventor in January, 2000, of a proprietary *Impatiens walleriana* selection identified as 3180C-1, not patented, as the female, or seed parent, with a proprietary *Impatiens walleriana* selection identified as 3154-1-3, not patented, as the male, or pollen parent. The cultivar Balolestop was discovered and selected by the Inventor as a flowering plant within the progeny of the stated cross in a controlled environment in Elburn, Ill.

Asexual reproduction of the new cultivar by terminal cuttings taken at Elburn, Ill. since February, 2000, has shown that the unique features of this new Impatiens are stable and reproduced true to type in successive generations of asexual reproduction.

SUMMARY OF THE INVENTION

The following traits have been repeatedly observed and are determined to be the unique characteristics of 'Balolestop'. These characteristics in combination distinguish 'Balolestop' as a new and distinct cultivar:

1. Compact, upright, outwardly spreading and mounded plant habit.
2. Freely branching growth habit.
3. Dark green-colored leaves.
4. Freely flowering habit.
5. Red purple and white bi-colored flowers that are fully double and positioned above the foliage.

Plants of the new Impatiens differ primarily from plants of the parent selections in flower color.

The new Impatiens can be compared to the *Impatiens walleriana* cultivar Stardust Lavender, disclosed in U.S. Pat. No. 5,986,188. However, in side-by-side comparisons conducted in West Chicago, Ill., plants of the new Impatiens differed from plants of the cultivar Stardust Lavender in the following characteristics:

1. Plants of the new Impatiens had longer branches with longer internodes than plants of the cultivar Stardust Lavender.
2. Plants of the new Impatiens were more freely flowering than plants of the cultivar Stardust Lavender.
3. Plants of the new Impatiens had fewer petals per flower than plants of the cultivar Stardust Lavender.
4. Flower color of plants of the new Impatiens was red purple and white bi-colored whereas flower color of plants of the cultivar Stardust Lavender was purple and white bi-colored.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ slightly from the color values cited in the detailed botanical description which accurately describe the colors of the new Impatiens. The photograph comprises a side perspective view of multiple flowering plants of 'Balolestop' grown in a container.

DETAILED BOTANICAL DESCRIPTION

The cultivar Balolestop has not been observed under all possible environmental conditions. The phenotype may vary somewhat with variations in environment such as temperature and light intensity without, however, any variance in genotype. The aforementioned photograph and following observations and measurements describe plants grown in West Chicago, Ill., under commercial practice in a polycarbonate-covered greenhouse with day temperatures ranging from 20 to 24° C., night temperatures ranging from 10 to 17° C. and light levels ranging from 4,000 to 6,000 footcandles. Rooted young plants were planted in containers and had been growing for about five to six weeks when the photographs and the description were taken.

In the following description, color references are made to The Royal Horticultural Society Colour Chart, 1995 Edition, except where general terms of ordinary dictionary significance are used.

Botanical classification:*Impatiens walleriana* cultivar Balolestop.

Parentage:

*Female parent.*—Proprietary *Impatiens walleriana* selection identified as 3180C-1, not patented.

*Male parent.*—Proprietary *Impatiens walleriana* selection identified as 3154-1-3, not patented.

Propagation:

*Type cutting.*—Terminal cuttings.

*Time to initiate roots.*—About 7 days at 18° C.

*Time to produce a rooted young plant.*—About 21 days at 18° C.

*Root description.*—Fibrous and fine.

*Rooting habit.*—Freely branching.

Plant description:

*General appearance.*—Compact, upright, outwardly spreading and mounded plant habit. Appropriate for 10-cm and larger containers.

*Growth and branching habit.*—Vigorous and freely-branching growth habit with about four basal branches and lateral branches potentially forming at every node; dense and bushy growth. Pinching, that is, removal of the terminal apices, is not required, but will enhance branching.

*Plant height.*—About 14.9 cm.

*Plant diameter or spread.*—About 26.2 cm.

*Lateral branches.*—Length: About 14.9 cm. Diameter: About 9 mm. Internode length: About 2.4 cm. Texture: Smooth, glabrous. Color: 146C.

*Foliage description.*—Arrangement: Opposite, simple. Length: About 4.8 cm. Width: About 2.8 cm. Shape: Ovate. Apex: Acuminate. Base: Attenuate. Margin: Serrate to crenate with ciliation. Texture, upper and lower surfaces: Smooth, glabrous. Venation pattern: Pinnate, arcuate. Color: Young and fully expanded foliage, upper surface: Between 146A and 147A. Young and fully expanded foliage, lower surface: Between 146B and 147B. Venation, upper and lower surfaces: 146B. Petiole: Length: About 1.3 cm. Diameter: About 1.9 mm. Texture, upper and lower surfaces: Smooth, glabrous. Color: 146D.

Flower description:

*Flower type and habit.*—Numerous and consistently double flowers. Flower buds open similar to a rose in fullness; flowers rounded in shape. Flowers arise from leaf axils. Freely flowering, usually about nine flowers and flower buds per lateral branch. Flowers positioned above the foliage and typically face upright or outward. Flowers last about five to seven days under greenhouse conditions. Flowers not persistent. Flowers not fragrant.

*Flowering season.*—Year-round under greenhouse conditions. In the garden, flowering is continuous from spring until fall.

*Flower size.*—Diameter: About 3.9 cm. Depth: About 1.4 cm.

*Flower buds* (*at stage of showing color*).—Length: About 1.2 cm. Diameter: About 8 mm. Shape: Ovoid. Color: 68B.

*Petals.*—Quantity/arrangement: About 17 per flower; imbricate. Length, largest petals: About 2 cm. Width, largest petals: About 1.5 cm. Shape: Obovate. Apex: Emarginate. Base: Truncate to attenuate. Margin: Entire. Texture, upper and lower surfaces: Velvety, smooth. Color: When opening, upper surface: 67B. When opening, lower surface: 54B. Fully opened, upper surface: Between 66B and 67B; overlain with white, 155D, spots and speckles; towards the base, 155D; main color becoming closer to 67C with subsequent development. Fully opened, lower surface: 54B; overlain with white, 155D, spots and speckles; towards the base, 155D.

*Sepals.*—Quantity/arrangement: Five in a single whorl; one modified into an elongated spur. Calyx length: About 1 cm. Calyx diameter: About 1 cm. Shape: Elliptic. Apex: Acute. Margin: Entire. Texture, upper and lower surfaces: Smooth, glabrous. Color, upper and lower surfaces: 144B. Spur length: About 3 cm. Spur color: 150C; towards the apex, 181B.

*Peduncles.*—Length: About 2 cm. Diameter: About 1.25 mm. Angle: Acute. Strength: Strong. Color: Close to 146C.

*Reproductive organs.*—None observed.

*Seed/fruit.*—None observed.

Disease/pest resistance: Plants of the new Impatiens have not been observed to be resistant to pathogens and pests common to Impatiens.

It is claimed:

1. A new and distinct cultivar of Double Impatiens plant named 'Balolestop', as illustrated and described.

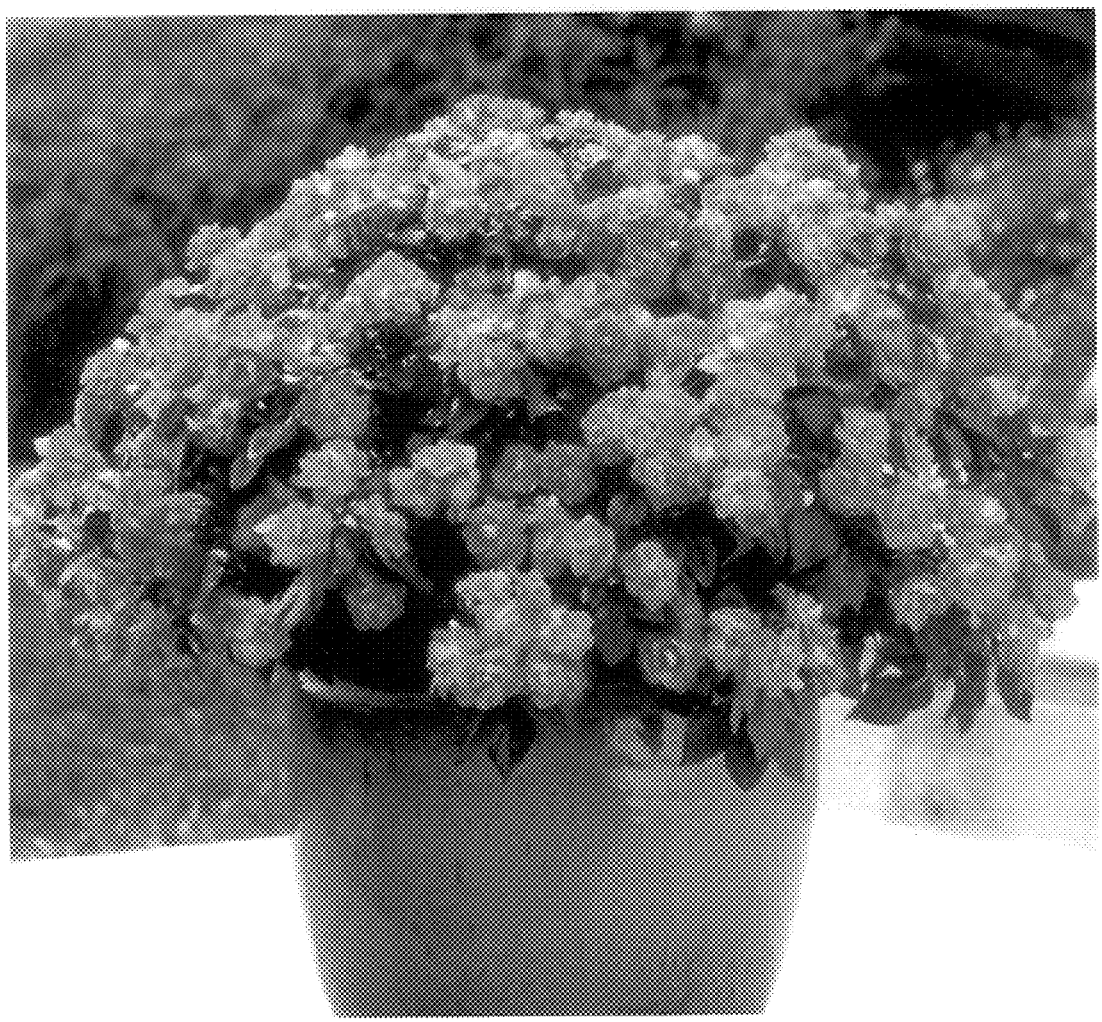

* * * * *